(12) United States Patent
Lu et al.

(10) Patent No.: US 11,986,462 B2
(45) Date of Patent: May 21, 2024

(54) USE OF TACROLIMUS IN PREPARATION OF MEDICAMENT FOR INITIATING TISSUE REGENERATION FUNCTION

(71) Applicant: Huiqiang Lu, Ganzhou (CN)

(72) Inventors: Huiqiang Lu, Ganzhou (CN); Yunlong Meng, Ganzhou (CN); Yong Huang, Ganzhou (CN); Fasheng Liu, Ganzhou (CN)

(73) Assignee: Huiqiang Lu, Jiangxi Province (CN)

( * ) Notice: Subject to any disclaimer, the term of this patent is extended or adjusted under 35 U.S.C. 154(b) by 36 days.

(21) Appl. No.: 17/479,869

(22) Filed: Sep. 20, 2021

(65) Prior Publication Data

US 2022/0087984 A1 Mar. 24, 2022

(30) Foreign Application Priority Data

Sep. 22, 2020 (CN) .......................... 202011002205.5

(51) Int. Cl.
*A61K 31/4353* (2006.01)
*A61K 9/08* (2006.01)
*A61K 31/436* (2006.01)
*A61K 47/20* (2006.01)

(52) U.S. Cl.
CPC ............... *A61K 31/436* (2013.01); *A61K 9/08* (2013.01); *A61K 47/20* (2013.01)

(58) Field of Classification Search
CPC .................................................. A61K 31/4353
See application file for complete search history.

(56) References Cited

FOREIGN PATENT DOCUMENTS

WO WO-2004044144 A2 * 5/2004 ......... A61K 31/4245

OTHER PUBLICATIONS

Daane, Jacob M., et al. "Bioelectric-calcineurin signaling module regulates allometric growth and size of the zebrafish fin." Scientific Reports (2018), vol. 8, pp. 1-9 of 9. (Year: 2018).*
First Chinese Office Action (with English translation) dated Apr. 22, 2021 for Chinese Appl. No. 202011002205.5.
Second Chinese Office Action (with English translation) dated Oct. 27, 2021 for Chinese Appl. No. 202011002205.5.
Kujawski et al; "Calcineurin Regulates Coordinated Outgrowth of Zebrafish Regenerating Fins"; Developmental Cell 28; Mar. 10, 2014; pp. 573-587.

* cited by examiner

*Primary Examiner* — John S Kenyon
(74) *Attorney, Agent, or Firm* — Ohlandt, Greeley and Perle, LLP

(57) ABSTRACT

The present disclosure belongs to the technical field of tissue regeneration, and specifically relates to use of tacrolimus in preparation of a medicament for initiating a tissue regeneration function. In the present disclosure, adding the tacrolimus may initiate the tissue regeneration of a non-regenerative distal caudal fin in a caudal fin resection experiment of a zebrafish. The present disclosure finds that tacrolimus inhibits the calcineurin activity and has a novel use for initiating the tissue regeneration of non-regenerative tissues. The present disclosure expands the use field of tacrolimus and has important value.

7 Claims, 2 Drawing Sheets

USE OF TACROLIMUS IN PREPARATION OF MEDICAMENT FOR INITIATING TISSUE REGENERATION FUNCTION

CROSS REFERENCE TO RELATED APPLICATION(S)

This patent application claims the benefit and priority of Chinese Patent Application No. 202011002205.5 filed on Sep. 22, 2020, the disclosure of which is incorporated by reference herein in its entirety as part of the present application.

TECHNICAL FIELD

The present disclosure belongs to the technical field of tissue regeneration, and specifically relates to use of tacrolimus in preparation of a medicament for initiating a tissue regeneration function.

BACKGROUND ART

Regeneration refers to a process of rebuilding lost body parts to restore mass and function thereof. Different animals have different regenerative capacities formed by long-term evolution of the animals. Generally, lower animals have a stronger tissue regenerative capacity than that of higher animals. For example, after a planarian is cut into multiple segments, each segment of which can regenerate a new individual with body parts including head and brain, due to its unique regenerating ability. Limbs of a salamander, and caudal fin and various tissues and organs of a zebrafish can still be regenerated after partial removal. However, human has extremely-limited regenerative capacity of tissues: only small wounds (skin or glands and the like) can be regenerated, and tissues and organs (extremities, heart and head and the like) with a larger area cannot be regenerated.

Tacrolimus (FK506) has a trade name of Prograf Tacrolimus is a macrolide antibiotic isolated from *Streptomyces* by Fujisawa Pharmaceutical Co., Ltd. Tacrolimus is extremely-unstable in aqueous solution and can be rapidly degraded, with a half-life of 10.7 h in the human body. FK506 is widely used to reduce or block immune rejection reactions commonly occurred in surgical transplantation, graft-versus-host disease and autoimmune disease treatment. At present, tacrolimus is mainly used for inhibiting rejection reactions of organ transplantation, promoting nerve regeneration and neuroprotection. However, use of tacrolimus in initiating the regeneration of non-regenerative tissues has not been found.

SUMMARY

To solve the above technical problem, the present disclosure provides use of tacrolimus in preparation of a medicament for initiating a tissue regeneration function.

Use of tacrolimus in preparation of a medicament for initiating a tissue regeneration function is provided.

In the present disclosure, the tissue may preferably be a distal caudal fin tissue of a zebrafish.

In the present disclosure, tacrolimus may preferably be used for preparing a regeneration agent of the distal caudal fin tissue of the zebrafish.

In the present disclosure, tacrolimus may preferably be used for preparing a calcineurin activity inhibitor.

In the present disclosure, tacrolimus may preferably be dissolved in dimethyl sulfoxide (DMSO) to prepare a medicament that can initiate the tissue regeneration or inhibit the activity of calcineurin.

In the present disclosure, tacrolimus may preferably have a stock solution with a concentration of 20 mM, and a working concentration of 3 µM.

In the present disclosure, tacrolimus may preferably be added to a culture solution of the zebrafish.

Compared with the prior art, the technical solutions of the present disclosure have the following beneficial effects:

Calcineurin is a serine/threonine phosphatase and a known regulator of the proportional growth of zebrafish fins. A low activity level of the calcineurin corresponds to a high fin regeneration rate, and inhibition of calcineurin activity changes fin position information by promoting retinoic acid (RA) signal to enhance fin regeneration. There is evidence that the calcineurin may regulate and coordinate growth. The present disclosure finds that the tacrolimus may inhibit the calcineurin activity and has a novel use for initiating the tissue regeneration of non-regenerative tissues. The present disclosure expands the use field of tacrolimus and has important value. In the present disclosure, adding tacrolimus may initiate the tissue regeneration of a non-regenerative distal caudal fin in a caudal fin resection experiment of the zebrafish.

DETAILED DESCRIPTION OF THE EMBODIMENTS

Figure 1:
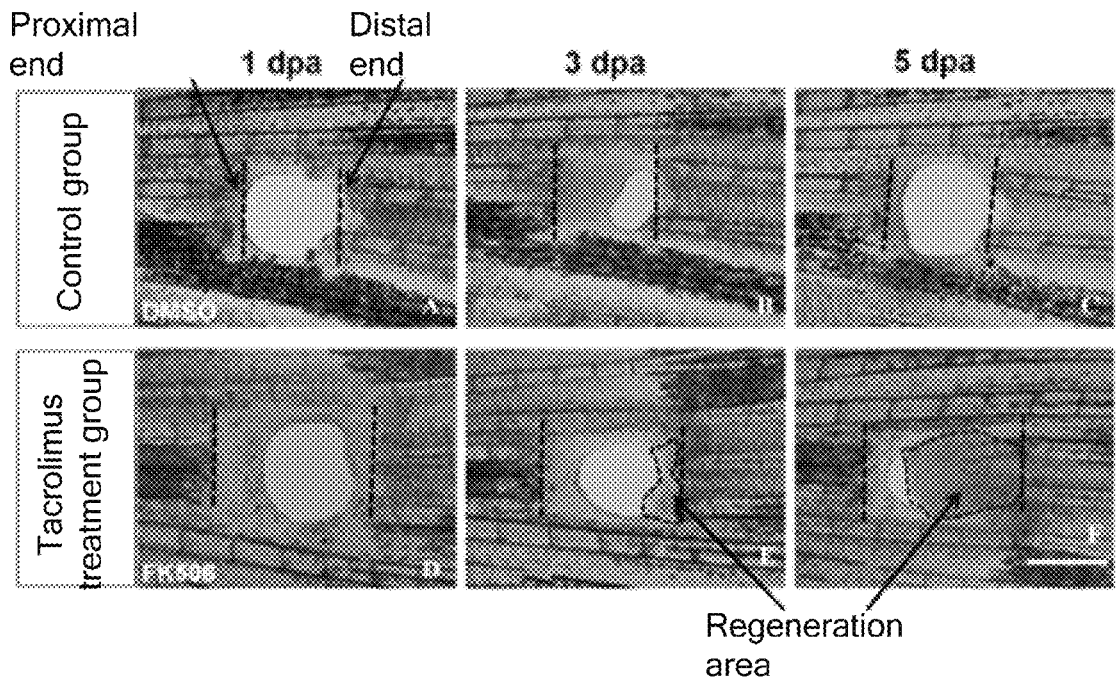
FIG. 1 is a regeneration status of proximal and distal tissues in a control group and a tacrolimus treatment group, where A to C in FIG. 1 are caudal fin tissues of the zebrafish at 1, 3 and 5 dpa (day after amputation) days after the construction of a wound model of the control group, respectively; D to F in FIG. Tare caudal fin tissues of the zebrafish at 1, 3 and 5 days after the construction of a wound model of the tacrolimus treatment group, respectively.

To enable a person skilled in the art to better understand the technical solutions of the present disclosure, the present disclosure is further described below in detail with reference to specific examples and accompanying drawings.

Example 1 A Tissue Regeneration Experiment of a Distal Caudal Fin of a Zebrafish 1. Experimental fish lines and culturing method are as follows: a wild-type (AB) fish was used as an experimental fish, stored in a flowing water tank at 28±0.5° C. with a pH=7±0.5, a conductivity of an aquaculture water was 450±50 S/m; and a photoperiod was 14 h of lighting and 10 h of darkness. Fresh sandworms were fed three times a day. Raising was conducted in accordance with the guidelines of the Ministry of Science and Technology of the People's Republic of China on the cultivation of experimental animals (2006); all fishes were kept under standard laboratory conditions.

2. Wound model construction is as follows: an adult zebrafish was lightly anesthetized in an anesthetic supplemented with tricaine and placed in a 1.5 g/100 mL agarose tank. A tissue with a length of 2-3 joints and a width of two fin rays on caudal fin surface was excavated using a scalpel blade; a hole was exposed on the caudal fin surface to form a damaged tissue containing a proximal wound and a distal wound. Proximal regenerative tissues were daily removed to prevent the hole from being filled. A regeneration status of the caudal fin was imaged and recorded using a Zeiss Discovery V20 microscope (Carl Zeiss, Germany).

3. Tacrolimus (FK506) treatment is as follows:

Tacrolimus (quality purity: 99.93%) was purchased from MCE (Med Chem Express, USA), prepared into a 20 mM mother liquor using DMSO and stored in a refrigerator at −40° C.

Tacrolimus treatment group: 20 mM of a tacrolimus stock solution was added to a culture solution to prepare a culture solution containing 3 µM tacrolimus to treat 10 zebrafishes, and the culture solution was changed every other day.

Control group: 10 zebrafishes were treated using a culture solution containing DMSO with a volume fraction of 0.015%, and the culture solution was changed every other day. The control group and the tacrolimus treatment group had the same ingredients of culture solution except for DMSO and tacrolimus.

4. Determination of calcineurin activity is as follows: the proximal and distal tissues of zebrafishes in the control group (DMSO treatment) and the tacrolimus treatment group were collected, respectively, to obtain a total of 40 samples, a protein concentration was detected according to a Coomassie Brilliant Blue kit; the calcineurin activity was detected using a calcineurin detection kit (ENZO, BML-AK804, USA), where the kit included a calcineurin, a calmodulin and a phosphorylated RII peptide substrate. Free phosphate in the sample was removed, the phosphorylated RII peptide was added, and the sample was incubated at 30° C. for 30 min. Malachite green as a phosphate indicator was added, and the amount of free phosphate in the sample was determined using a SpectraMax® iD3 multi-mode microplate reader (Molecular Devices, USA). The calcineurin activity was normalized to a total protein concentration.

5. Results are as follows:

(1) FIG. 1 is a regeneration status of proximal and distal tissues in the control group and the tacrolimus treatment group. Under normal conditions (control group), tissues could only grow in the proximal wound, but never grew in the distal wound, shown in A to C in FIG. 1. B in FIG. 1 showed that a lot of new tissues could grow from the proximal wound on the third day in that the proximal regenerative tissues were not completely removed on the second day after the caudal fin tissue was removed. D to F in FIG. 1 showed that the non-regenerative distal tissues regenerate tissues after tacrolimus was added, indicating that the distal tissue regeneration was initiated after tacrolimus treatment.

Figure 2:
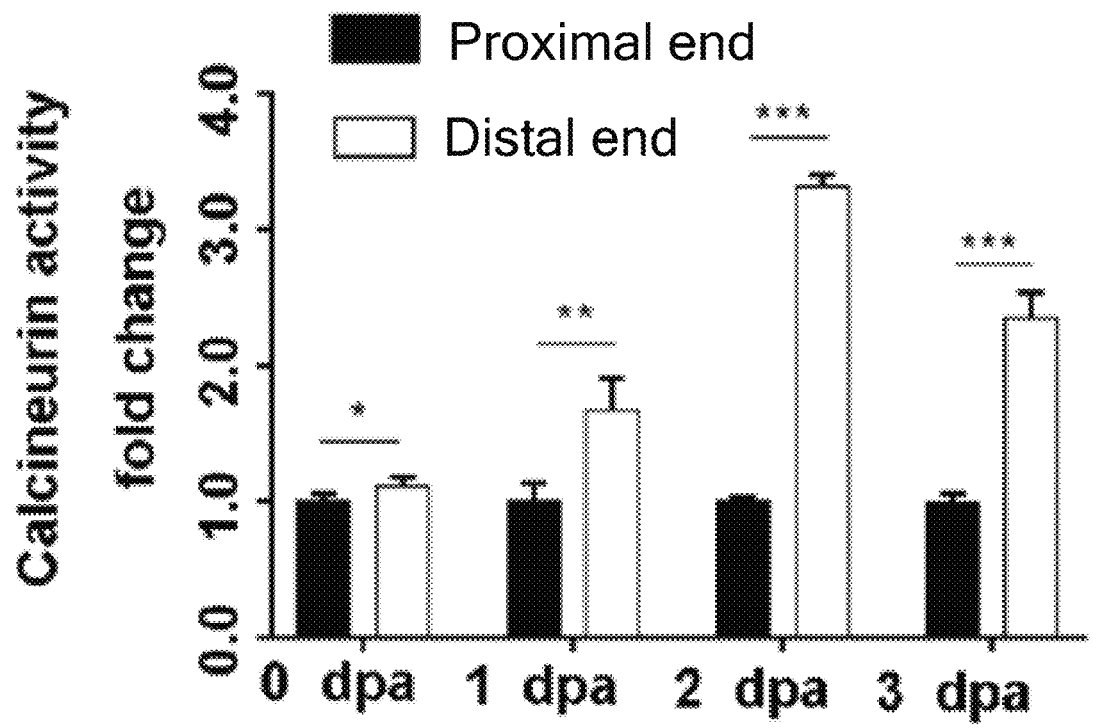
FIG. 2 is a detection result of calcineurin activity in the control group.
Figure 3:
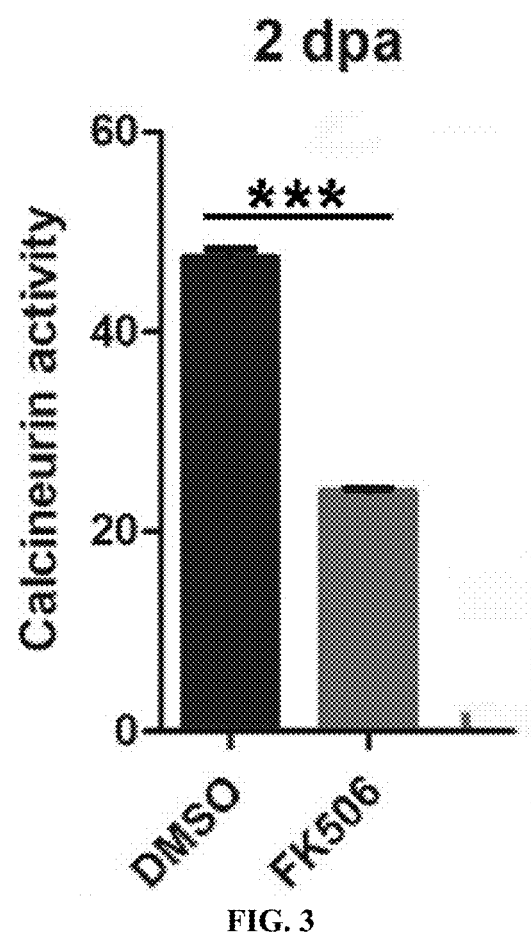
FIG. 3 is a detection result of calcineurin activity in the tacrolimus treatment group.

(2) FIG. 2 is the detection result of calcineurin activity in the control group, and FIG. 3 is the detection result of calcineurin activity in the tacrolimus treatment group. The results showed that in the normally-regenerated caudal fin, the calcineurin activity in the distal tissue was higher than that in the proximal tissue. The calcineurin activity in the tissues that had initiated regeneration (FK506 experimental group) was lower than that of the non-regenerative tissues (DMSO control group) under normal conditions after tacrolimus was added. Significance analysis is: *$P<0.05$, $P<0.01$, and *$P<0.001$, mean±standard deviation.

It should be noted that when a numerical range is involved in the present disclosure, it shall be understood that the two end points of each numerical range and any value between the two end points can be selected. Since the steps and methods used are the same as those in the examples, the present disclosure describes the preferred example in order to prevent repetition. Although some preferred examples of the present disclosure have been described, persons skilled in the art can make changes and modifications to these examples once they learn the basic inventive concept. Therefore, the appended claims are intended to be interpreted as including the preferred examples and all changes and modifications falling within the scope of the present disclosure.

Obviously, those skilled in the art can make various changes and modifications to the present disclosure without departing from the spirit and scope of the present disclosure. In this way, if these modifications and variations of the present disclosure fall within the scope of the claims of the present disclosure and equivalent technologies thereof, the present disclosure is further intended to include these modifications and variations.

What is claimed is:

1. A method for initiating a tissue regeneration function of a distal caudal fin tissue of a zebrafish, the distal caudal fin tissue lacking a regeneration function and having a hole therein, comprising administering to the distal caudal fin tissue a medicament comprising tacrolimus as an active component, wherein the medicament initiates regeneration of the distal caudal fin tissue from a distal end to a proximal end.

2. The method according to claim 1, wherein tacrolimus is used for preparing a regeneration agent of the distal caudal fin tissue of the zebrafish.

3. The method according to claim 1, wherein tacrolimus is used for preparing a calcineurin activity inhibitor.

4. The method according to claim 1, wherein tacrolimus is dissolved in dimethyl sulfoxide (DMSO) to prepare a liquid medicament.

5. The method according to claim 4, wherein tacrolimus has a stock solution with a concentration of 20 mM, and a working concentration of 3 µM.

6. The method according to claim 5, wherein tacrolimus is added to a culture solution of the zebrafish.

7. The method according to claim 4, wherein tacrolimus is used for preparing a calcineurin activity inhibitor.

* * * * *